(12) United States Patent
McCormick

(10) Patent No.: US 10,966,764 B2
(45) Date of Patent: Apr. 6, 2021

(54) KNOTLESS SUTURE LOCKING BONE PLATE

(71) Applicant: Wright Medical Technology, Inc., Memphis, TN (US)

(72) Inventor: Daniel F. McCormick, North Kingstown, RI (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 175 days.

(21) Appl. No.: 16/004,587

(22) Filed: Jun. 11, 2018

(65) Prior Publication Data

US 2018/0353228 A1  Dec. 13, 2018

Related U.S. Application Data

(60) Provisional application No. 62/518,312, filed on Jun. 12, 2017.

(51) Int. Cl.
| | | |
|---|---|---|
| *A61B 17/80* | (2006.01) | |
| *A61B 17/84* | (2006.01) | |
| *A61B 17/68* | (2006.01) | |
| *A61B 17/06* | (2006.01) | |
| *A61B 17/04* | (2006.01) | |

(52) U.S. Cl.
CPC ...... *A61B 17/8004* (2013.01); *A61B 17/0401* (2013.01); *A61B 17/06166* (2013.01); *A61B 17/8061* (2013.01); *A61B 17/84* (2013.01); *A61B 17/683* (2013.01); *A61B 17/842* (2013.01); *A61B 2017/0414* (2013.01); *A61B 2017/0417* (2013.01); *A61B 2017/0437* (2013.01); *A61B 2017/0448* (2013.01); *A61B 2017/0454* (2013.01); *A61B 2017/0459* (2013.01)

(58) Field of Classification Search
CPC ... A61B 17/80; A61B 17/06; A61B 17/06166; A61B 17/0466; A61B 17/82; A61B 17/0401; A61F 2/0811
See application file for complete search history.

(56) References Cited

U.S. PATENT DOCUMENTS

| | | | |
|---|---|---|---|
| 7,857,836 | B2 | 12/2010 | Huebner et al. |
| 8,267,973 | B2 | 9/2012 | Humphrey |
| 8,475,504 | B2 | 7/2013 | Gillard et al. |
| 8,535,313 | B1 | 9/2013 | Masson |
| 9,414,871 | B2 | 8/2016 | Huebner et al. |

(Continued)

*Primary Examiner* — David W Bates
(74) *Attorney, Agent, or Firm* — Duane Morris LLP

(57) ABSTRACT

A syndesmosis system includes a bone plate and an anchor. The bone plate includes a body extending between first and second surfaces. The body defines a strand-locking hole extending from the first surface to the second surface. A first locking element and a second locking element each extend from a first side wall of the strand-locking hole to a second side wall of the strand-locking hole. Each of the first anchor and the second anchor extend transverse to a central axis of the anchor hole. The anchor includes a body defining a first wing and a second wing. The first and second wings are coupled at a distal end and are biased away from a longitudinal axis of the body. The first and second wings are configured to maintain the anchor in a fixed position when inserted into a hole formed in a bone.

18 Claims, 8 Drawing Sheets

(56) References Cited

U.S. PATENT DOCUMENTS

| | | |
|---|---|---|
| 9,480,475 B2 | 11/2016 | Conley et al. |
| 2006/0135958 A1 | 6/2006 | Marissen et al. |
| 2009/0118776 A1* | 5/2009 | Kelsch ............... A61B 17/0401 606/325 |
| 2013/0030480 A1* | 1/2013 | Donate .............. A61B 17/0401 606/328 |
| 2013/0197575 A1 | 8/2013 | Karapetian et al. |
| 2013/0197579 A1 | 8/2013 | Foerster et al. |
| 2014/0025123 A1* | 1/2014 | Zeetser ................. A61B 17/82 606/289 |
| 2014/0052176 A1* | 2/2014 | Conley .............. A61B 17/0401 606/232 |
| 2014/0128921 A1 | 5/2014 | Parsons et al. |
| 2014/0142627 A1 | 5/2014 | Hendricksen et al. |
| 2015/0032134 A1* | 1/2015 | Mercelis ........... A61B 17/0401 606/151 |
| 2015/0201929 A1* | 7/2015 | Dooney, Jr. ........ A61B 17/0401 606/225 |
| 2016/0100932 A1* | 4/2016 | Kumar ................... A61B 17/80 606/70 |
| 2016/0213368 A1* | 7/2016 | Stecco ............. A61B 17/06166 |

\* cited by examiner

KNOTLESS SUTURE LOCKING BONE PLATE

This application claims the benefit of priority of U.S. Provisional Patent Application No. 62/518,312, filed Jun. 12, 2017 of which is expressly incorporated herein by reference in its entirety.

BACKGROUND

Various injuries include separation of soft tissue from one or more bones and/or separation of bones from normally anatomical correct positioning. Maintaining the bones in the correct anatomical positions during healing is important to provide proper soft tissue reattachment and proper bone healing. For example, during syndesmosis repair, a first bone and a second bone must be maintained in a fixed position to allow the connective tissue to heal.

Current suture systems include one or more knots for maintaining sutures in a fixed position. Knots formed on the sutures can cause irritation during healing and may be subject to tearing due to friction or other forces applied to the knot. Current systems further require surgeons to form knots during surgery. Such systems are prone to failure and increase time of surgery.

SUMMARY

In various embodiments, a system is disclosed. The system includes an anchoring device and an anchor. The anchoring device includes a body extending between a first surface and a second surface. The body defines a strand-locking hole extending from the first surface to the second surface. A first locking element and a second locking element each extend from a first side wall of the strand-locking hole to a second side wall of the strand-locking hole. Each of the first anchor and the second anchor extend transverse to a central axis of the anchor hole. The anchor includes a body defining a first wing and a second wing. The first and second wings are coupled at a distal end and biased away from a longitudinal axis of the body. The first and second wings are configured to maintain the anchor in a fixed position when the anchor is inserted into a hole formed in a bone.

In various embodiments, a method of syndesmosis is disclosed. The method includes forming a bone tunnel through a first bone and a second bone and passing at least one flexible strand through the bone tunnel from a first side to a second side. The at least one flexible strand is coupled to an anchor including a body defining a first wing and a second wing coupled at a distal end and biased away from a longitudinal axis of the body. The body is sized and configured for insertion into a first side of the bone tunnel. The at least one flexible strand is passed through a locking hole formed in a bone plate. The bone plate is configured to abut a surface of the second bone defining the second side of the bone tunnel. The first bone and the second bone are positioned at a predetermined spacing by applying a tensioning force to the at least one flexible strand. The at least one flexible strand is locked at a predetermined length. The at least one flexible strand is locked by a first locking element and a second locking element positioned within the locking hole formed in the bone plate.

In various embodiments, a system is disclosed. The system includes a bone plate, an anchor, and a flexible strand extending between the bone plate and the anchor. The bone plate includes a body extending between a first surface and a second surface and defining a strand-locking hole extending from the first surface to the second surface. A first locking element and a second locking element each extend from a first side wall of the strand-locking hole to a second side wall of the strand-locking hole. Each of the first locking element and the second locking element extend transverse to a central axis of the anchor hole. The anchor includes a body defining a first wing and a second wing that are coupled at a distal end and biased away from a longitudinal axis of the body. The first and second wings are configured to maintain the anchor in a fixed position when the anchor is inserted into a hole formed in a bone. The anchor includes a coupling extension extending from the distal end of the first wing and the second wing and defining at least one hole extending therethrough. A first end of the flexible strand is coupled to the at least one hole formed in the coupling extension of the anchor and a second end of the flexible strand extends beneath the second locking element, between the first locking element and the second locking element, and above the first locking element of the bone plate.

BRIEF DESCRIPTION OF THE FIGURES

The features and advantages of the present invention will be more fully disclosed in, or rendered obvious by the following detailed description of the preferred embodiments, which are to be considered together with the accompanying drawings wherein like numbers refer to like parts and further wherein.

DETAILED DESCRIPTION

Figure 1:
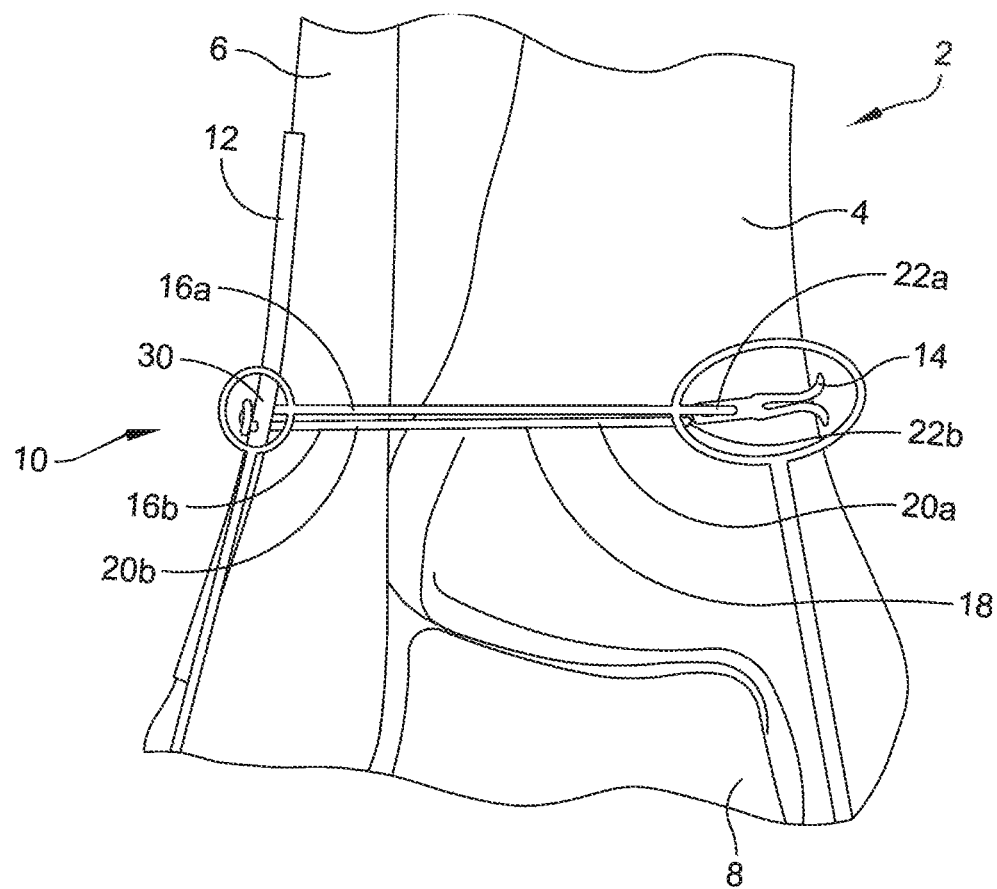
FIG. 1 illustrates a joint including a first bone and a second bone coupled by at least one flexible strand extending between a bone plate and an anchor, in accordance with some embodiments.

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top," "bottom," "proximal," "distal," "superior," "inferior," "medial," and "lateral" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected," refer to a relationship wherein structures are secured or attached to one another either directly or indirectly through intervening structures, as well as both movable or rigid attachments or relationships, unless expressly described otherwise.

FIG. 1 illustrates a joint 2 including a first bone 4 and a second bone 6 coupled by at least one flexible strand 16a, 16b extending between a bone plate 12 and an anchor 14, in accordance with some embodiments. In some embodiments, the joint 2 is an ankle joint including a tibia 4, a fibula 6, and a talus 8. An anchoring construct 10 includes a bone plate 12 and an anchor 14 having at least one flexible strand 16a, 16b extending therebetween. The flexible strands 16a, 16b can include any suitable material, such as one or more sutures, threads, ribbons, and/or any other suitable flexible material. The flexible strands 16a, 16b extend through a bone tunnel 18 having a first portion 20a extending through the first bone 4 and a second portion 20b extending through the second bone 6. The first and second portions 20a, 20b can be aligned along a common longitudinal axis (as shown in FIG. 1) and/or can be offset.

In some embodiments, the flexible strands 16a, 16b of the anchoring construct 10 can be adjusted (e.g., shortened) to apply a tensioning force to the first bone 4 and the second bone 6 to position the first bone 4 and the second bone 6 in a predetermined spaced relationship. In some embodiments, the predetermined spaced relationship is selected to mimic a natural spacing of the first bone 4 and the second bone 6. The flexible strands 16a, 16b allow the first bone 4 and the second bone 6 to be maintained in the predetermined spaced relationship while allowing natural range of movement between the first bone 4 and the second bone 6.

In some embodiments, the flexible strands 16a, 16b can be locked after adjustment to maintain the first bone 4 and the second bone 6 in the predetermined spaced relationship. For example, in the illustrated embodiment, a first end 22a of each of the flexible strands 16a, 16b is fixedly coupled to an anchor 14 coupled to the first bone 4. The first end 22a of the flexible strands 16a, 16b can be coupled to the anchor 14 using any suitable coupling mechanism. For example, in some embodiments, the flexible strands 16a, 16b can be inserted through one or more holes formed in the anchor 14, as described in greater detail below. A knot can be formed at the first end 22a of each of the flexible strands 16a, 16b to prevent the flexible strands 16a, 16b from passing back through the one or more holes formed in the anchor 14. In other embodiments, the flexible strands 16a, 16b can be coupled to the anchor 14 using a crimp and/or other compression coupling. Although specific embodiments are discussed herein, it will be appreciated that the flexible strands 16a, 16b can be coupled to the anchor 14 using any suitable coupling mechanism.

In some embodiments, a second end 22b of each of the flexible strands 16a, 16b is passed through a strand-locking hole 50 formed in the bone plate 12. The strand-locking hole 50 is configured to prevent movement (e.g., lengthening/shortening) of the flexible strands 16a, 16b when a predetermined tension is applied to the flexible strands 16a, 16b. In some embodiments, the predetermined tension corresponds to a predetermined spacing of the first bone 4 and the second bone 6. The strand-locking hole 50 can include one or more locking elements configured to lock the first strand 16a and/or the second strand 16b in a fixed position when the predetermined tension is applied to the flexible strands 16a, 16b, as discussed in greater detail below with respect to FIGS. 2-5.

Figure 2:
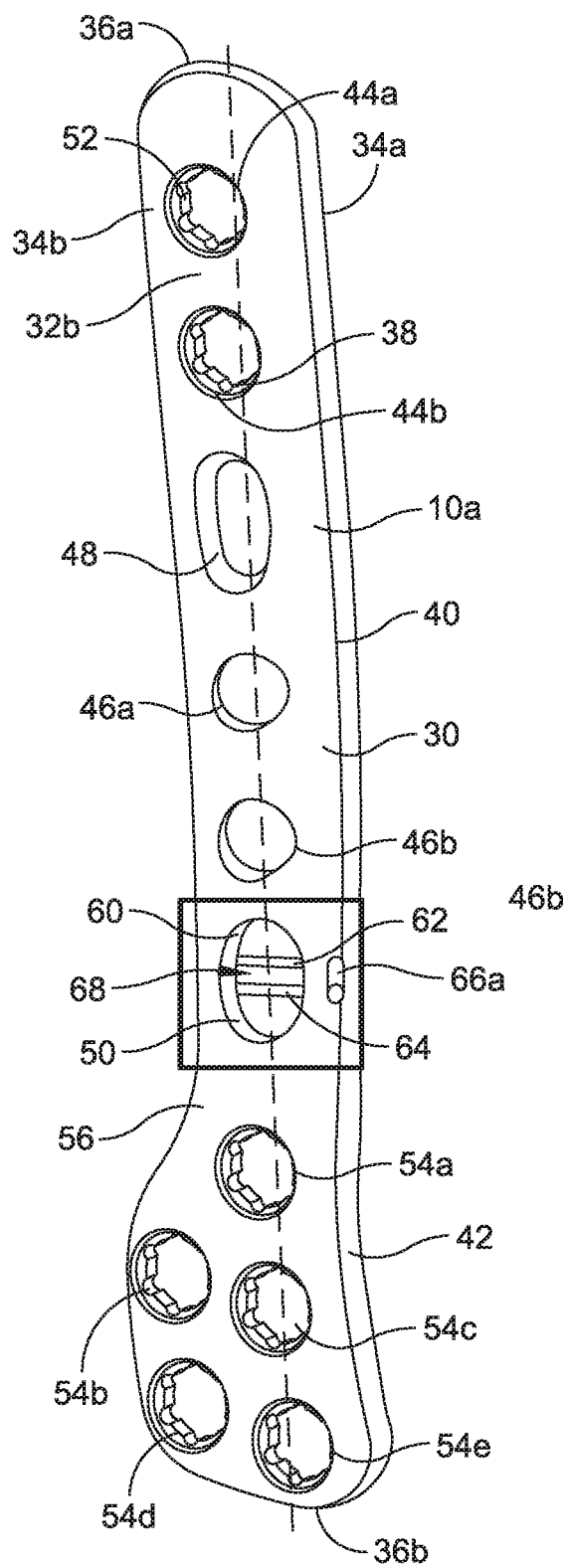
FIG. 2 illustrates a bone plate including at least one strand-locking hole, in accordance with some embodiments.

FIG. 2 illustrates a bone plate 12a including at least one locking hole 50a, in accordance with some embodiments. The bone plate 12a is similar to the bone plate 12 discussed above, and similar description is not repeated herein. The bone plate 12a includes a body 30 extending between a bone-contacting surface 32a and an opposed, outer surface 32b. A perimeter of the bone plate is defined by a first side edge 34 and a second side edge 34b extending generally along a longitudinal axis 38 of the bone plate 12a and a top edge 36a and a bottom edge 36b generally extending perpendicular to the longitudinal axis 38. The body 30 has a predetermined thickness between the bone-contacting surface 32a and the outer surface 32b.

In some embodiments, the body 30 includes a shaft portion 40 and a head portion 42. The shaft portion 40 extends generally along a longitudinal axis 38 of the bone plate 12a and is sized and configured to conform to a portion of the second bone 6, such as, for example, a diaphysis of the second bone 6. The shaft portion 40 has a first width. The shaft portion 40 can include one or more locking fastener holes 44a-44b, non-locking fastener holes 46a-46b, slots 48, and/or strand-locking holes 50a. Although embodiments are discussed herein having locking fastener holes 44a-44b, non-locking fastener holes 46a-46b, and compression slots 48, it will be appreciated that the bone plate can include any combination of locking fastener holes 44a-44b, non-locking fastener holes 46a-46b, and slots 48 and is within the scope of this disclosure.

In some embodiments, each of the locking fastener holes 44a-44b includes a circumferential opening extending from the bone-contacting surface 32a to the outer surface 32b. An interrupted thread 52 extends at least partially therethrough. The interrupted thread 52 is formed by tapping a continuous thread into the locking fastener holes 44a-44b and forming one or more interruptions (or cutouts) 54 through the thread. The interrupted thread 52 is configured to allow a locking fastener to be inserted into the locking fastener holes 44a-44b at a variable, user-selected angle, to lock the bone plate 12a to a bone, such as the second bone 6.

In some embodiments, each of the non-locking fastener holes 46a-46b include a circumferential opening having a smooth side surface extending from the bone-contacting surface 32a to the outer surface 32b. The non-locking fastener holes 46a-46b are configured to receive a non-locking fastener therein. The non-locking fastener is coupled to a bone, such as the second bone 6, to pull the bone-contacting surface 32a of the bone plate 12a into contact with an outer surface of the bone 6. In some embodiments, the non-locking fastener holes 46a-46b are omitted.

In some embodiments, a slot 48 includes an oblong opening having a smooth side surface extending from the bone-contacting surface 32a to the outer surface 32b. The slot 48 is sized and configured to receive a non-locking fastener therein. The non-locking fastener can be variably positioned within the slot 48 and coupled to a bone.

In some embodiments, the shaft portion 40 is coupled to a head portion 42 at a lower end of the shaft portion 40. The head portion 42 has a second width. In some embodiments, the second width of the head portion 42 is greater than the first width of the shaft portion 40. The head portion 42 can be configured to conform to a portion of the second bone 6, such as a metaphysis of the second bone 6. In some embodiments, the head portion 42 can include a plurality of locking fastener holes, non-locking fastener holes, and/or slots extending from the bone-contacting surface 32a to the outer surface 32b. For example, in the illustrated embodiment, the bone plate 12a defines five locking fastener holes 54a-54e extending therethrough, although it will be appreciated that a greater and/or lesser number of locking fastener holes and/or one or more non-locking fastener holes or slots can be formed through the head portion 42. The locking fastener holes 54a-54e are similar to the locking fastener holes 44a-44b formed through the shaft portion 40, and similar description is not repeated herein.

In some embodiments, the head 42 of the bone plate 12a is offset from the shaft 40 by an offset portion 56. The shaft 40 is substantially disposed in a first plane and the head 42 is substantially disposed in a second plane. The offset portion 56 extends from the shaft 40 (e.g., the first plane) to the head 42 (e.g., the second plane) at a predetermined angle. The offset portion 56 positions an outer surface 32b of the head 42 above an outer surface 32b of the shaft 40 and the bone contacting surface 32a of the head 42 above the bone contacting surface 32a of the shaft 40. In some embodiments, the offset portion 56 positions the bone contacting surface 32a of the head 42 above the outer surface 32b of the shaft 40. In some embodiments, the offset portion 56 is configured to position the shaft 40 and the head 42 such that the bone plate 12a conforms to an outer surface of a bone, such as, a lateral side of a fibula, a medial side of a tibia, and/or any other suitable bone. The bone plate 10a can be coupled to the second bone 6 using any combination of locking and/or non-locking fasteners inserted through any combination of locking holes 44a-44b, 54a-54b, non-locking holes 46a-46b, and/or slots 48.

In some embodiments, the bone plate 12a includes at least one strand-locking hole 50a. A strand-locking hole 50a can extend through any portion of the plate 12a, such as the shaft 40, the head 42, and/or the offset portion 56. The strand-locking hole 50a is sized and configured to receive a flexible strand, such as flexible strands 16a, 16b, therethrough. The strand-locking hole 50a includes a locking element 60 including one or more locking elements 62, 64 configured to lock a flexible strand 16a, 16b in a fixed position when a predetermined tension is applied to the flexible strand 16a, 16b.

Figure 3:
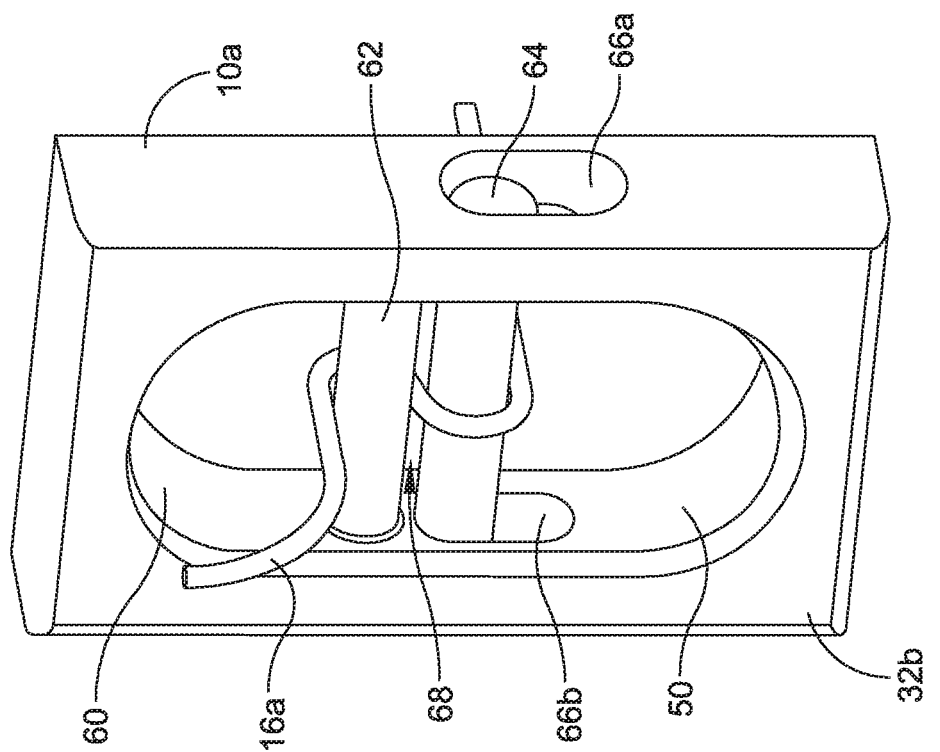
FIG. 3 illustrates an expanded view of the strand-locking hole of the bone plate of FIG. 2, in accordance with some embodiments.

FIG. 3 illustrates an expanded view of the strand-locking hole 50a of the bone plate 12a, in accordance with some embodiments. The strand-locking hole 50a extends hole 50a from the bone contacting surface 32a to the outer surface 32b. The strand hole 50a can include any suitable shape, such as a circular, oblong, square, and/or any other suitable shape. In some embodiments, a locking element 60 is disposed within the strand-locking hole 50a. The locking element 60 includes a first locking element 62 and a second locking element 64 extending from a first side 60a of the strand hole 50a to a second side 60b of the strand hole 50a. For example, in some embodiments, the first locking element 62 and the second locking element 64 include beams or pins extending from the first side 60a to a second side 60b of the strand hole 50a and that are transverse to a central axis 61 of the strand hole 50a. The first locking element 62 and the second locking element 64 are configured to lock a flexible strand 16a, 16b in a fixed position when a predetermined tension is applied.

In some embodiments, the first locking element 62 is a fixed locking element having a fixed position within the strand hole 50a and the second locking element 64 is a moveable locking element having a variable position within the strand hole 50a. The second locking element 64 is configured to be transitioned from a first, unlocked position to a second, locked position. For example, in the illustrated embodiment, the second locking element 64 is disposed within a first channel 66a and a second channel 66b extending through the first side 60a and the second side 60b of the strand hole 50a, respectively. The second locking element 64 is configured to transition from a first end of each of the channels 66a, 66b to a second end of each of the channels 66a, 66b when a predetermined force is applied to the second locking element 64. The predetermined force can be applied to the second locking element 64 by the at least one flexible strand 16a, 16b. When the second locking element 64 is transitioned to a second end of the channels 66a, 66b, a retention element (not shown) is configured to lock and/or fix the second locking element 64 at the second end of the channels 66a, 66b. The retention element can include any suitable element, such as a notch, a hook, an adhesive, a mechanical retention element, and/or any other suitable retention element.

The flexible strand 16a can extend through the bone tunnel 18 from an anchor 14 coupled to the first bone 4, as discussed above. The flexible strand 16a, 16b can further be passed through the strand-locking hole 50a in a locking arrangement with the first locking element 62 and/or the second locking element 64. In some embodiments, at least one flexible strand, such as flexible strand 16a, extends through the strand hole 50a from the bone contacting surface 32a to the outer surface 32b below the second locking element 64. The flexible strand 16a is returned through the strand hole 50a from the outer surface 32b to the bone contacting surface 32a in a gap 68 between the first locking element 62 and the second locking element 64 such that the flexible strand 16a loops around the second locking element 64. The flexible strand 16a extends a second time through the strand hole 50a from the bone contacting surface 32a to the outer surface 32b above the first locking element 62. Although specific embodiments are discussed herein, it will be appreciated that the flexible strands 16a, 16b can be coupled to the locking elements 62, 64 in any suitable locking arrangement.

In use, a tensioning force is applied to a proximal end 22b of the flexible strand 16a. The tensioning force initially causes the flexible strand 16a to advance through the locking hole 50 and reduce the spacing between the first bone 4 and the second bone 6. For example, in some embodiments, the first end 22a of the flexible strand 16a, 16b is coupled to the first bone 4 by the anchor 14. As the flexible strand 16a, 16b is advanced through the strand-locking hole 50a (for example, by the tensioning force) the spacing between the first bone 4 and the second bone 6 is reduced. As the first bone 4 and the second bone 6 are adjusted, a force applied by the flexible strand 16a to the second locking element 64 increases. When the force exceeds a predetermined threshold, the second locking element 64 moves from the first, unlocked position to the second, locked position. In the unlocked position, the flexible strand 16a is capable of advancing through the locking hole. The second locking element 64 is retained in the locked position by a retention element (not shown).

Figure 4:
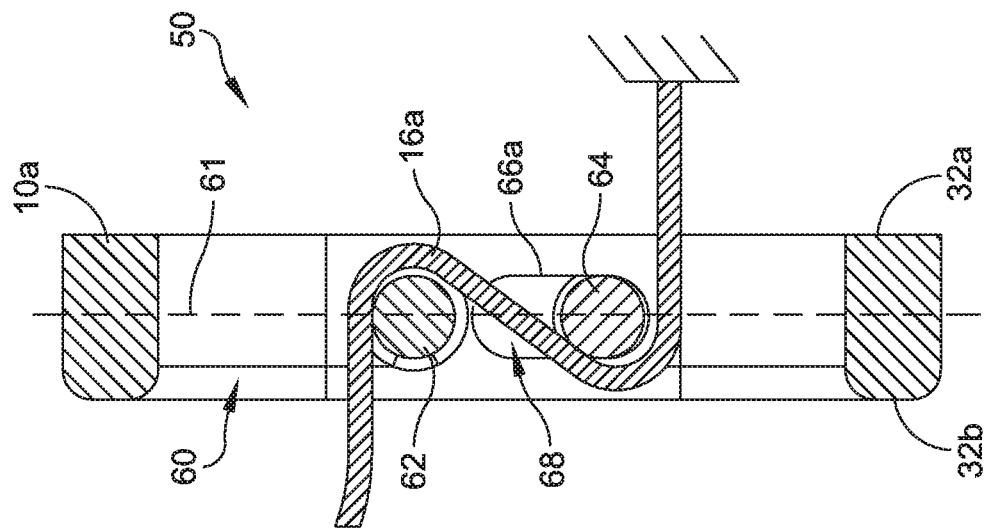
FIG. 4 illustrates a cross-sectional view of the strand-locking hole taken along line A-A of FIG. 3, in accordance with some embodiments.
Figure 5:
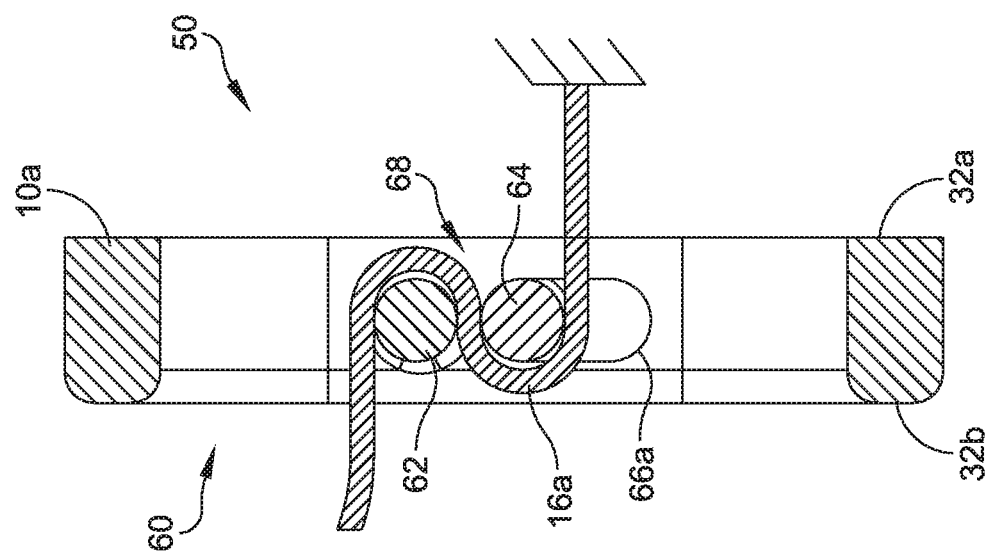
FIG. 5 illustrates the cross-sectional view of FIG. 4 having a second locking element in a second, locked position, in accordance with some embodiments.

When the second locking element 64 transitions to the second, locked position, the flexible strand 16a is prevented from moving through the strand-locking hole 50a. For example, as shown in FIG. 4, a flexible strand 16a extends through a gap 68 between the first locking element 62 and the second locking element 64. In the first position, the gap 68 has a first spacing and is configured to allow free movement of the flexible strand 16a. When the force applied by the flexible strands 16a, 16b exceeds the predetermined threshold, the second locking element 64 transitions to the second position, as shown in FIG. 5. In the second position, the gap 68 is reduced to a spacing less than the thickness of the flexible strand 16a such that the flexible strand 16a is compressed and locked between the first locking element 62 and the second locking element 64. In some embodiments, the predetermined threshold corresponds to a predetermined spacing of the first bone 4 and the second bone 6.

Although embodiments are discussed herein including a bone plate 12, 12a, it will be appreciated that the locking element 60 can be positioned within any suitable anchoring body configured to be coupled to the first bone 4 and/or the second bone 6. For example, in various embodiments, a locking element 60 can be disposed within a capsule anchor configured to be at least partially inserted into the first bone 4 and/or the second bone 6. In other embodiments, the locking element 60 can be positioned within an opening defined by a flat button and/or other fastener configured to be positioned against an outer surface of the first bone 4 and/or the second bone 6. It will be appreciated that the locking element 60 can be positioned within any suitable structure and/or body, and is within the scope of this disclosure.

Figure 6:
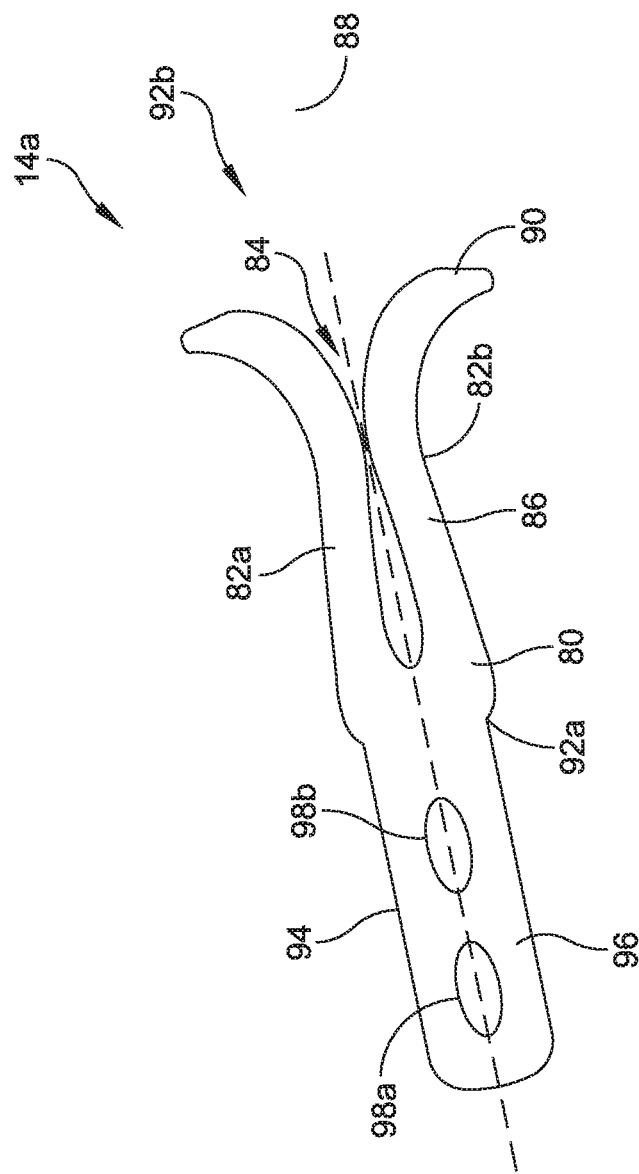
FIG. 6 illustrates an anchor, in accordance with some embodiments.
Figure 7:
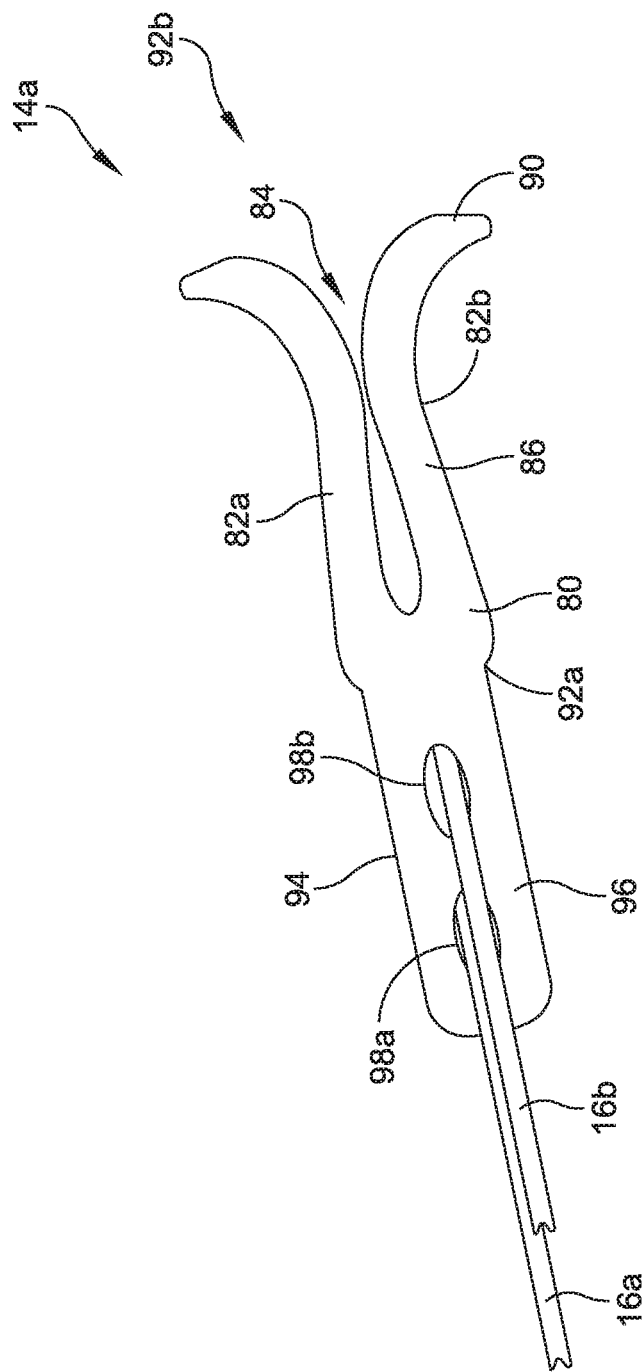
FIG. 7 illustrates the anchor of FIG. 6 having a first flexible strand and a second flexible strand coupled thereto, in accordance with some embodiments.

FIGS. 6-7 illustrates an anchor 14a, in accordance with some embodiments. The anchor 14a is similar to the anchor 14, and similar description is not repeated herein. The anchor 14a includes a body 80 defining a first wing 82a and a second wing 82b defining a slot 84 therebetween. The first wing 82a and the second wing 82b each define a longitudinal section 86 extending generally along a longitudinal axis 88 and a lateral section 90 extending at an angle with respect to the longitudinal axis 88. In some embodiments, the lateral sections 90 extend at a substantially 90° angle, although it will be appreciated that the lateral sections 90 can have a greater and/or lesser angle.

In some embodiments, the first wing 82a and the second wing 82b are biased in opposite directions. For example, in some embodiments, the first wing 82a and the second wing 82b are coupled at a distal end 92a and are separated by a slot 84 at a proximal end 92b such that the first wing 82a and the second wing 82b can be compressed towards each other. In use, the first wing 82a and the second wing 82b are compressed towards a center line 88 for insertion into a bone tunnel 18a. After insertion, the first wing 82a and the second wing 82b expand apart and apply a force to an inner surface of the bone tunnel 18a to maintain the anchor 14a in a fixed position within the bone tunnel 18a.

In some embodiments, a strand anchoring extension 94 extends from the distal end 92a of the body 80. The strand anchoring extension 94 includes a substantially flat body 96 extending from body 80a substantially along the longitudinal axis 88. The strand anchoring extension 94 is configured to couple one or more flexible strands 16a, 16b to the body 80. For example, in the illustrated embodiment, the strand anchoring extension 94 defines a plurality of anchoring holes 98a, 98b extending through the flat body 96. A distal end 22b of the flexible strands 16a, 16b extend through the anchoring holes 98a, 98b. A knot can be formed at the distal end 22b of the flexible strands 16a, 16b to prevent the flexible strands 16a, 16b from passing back through the anchoring holes 98a, 98b. In other embodiments, the strand anchoring extension can include a peg, screw, knotless coupling element and/or any other suitable anchor for coupling the flexible strands 16a, 16b to the strand anchoring extension 94.

Figure 8:
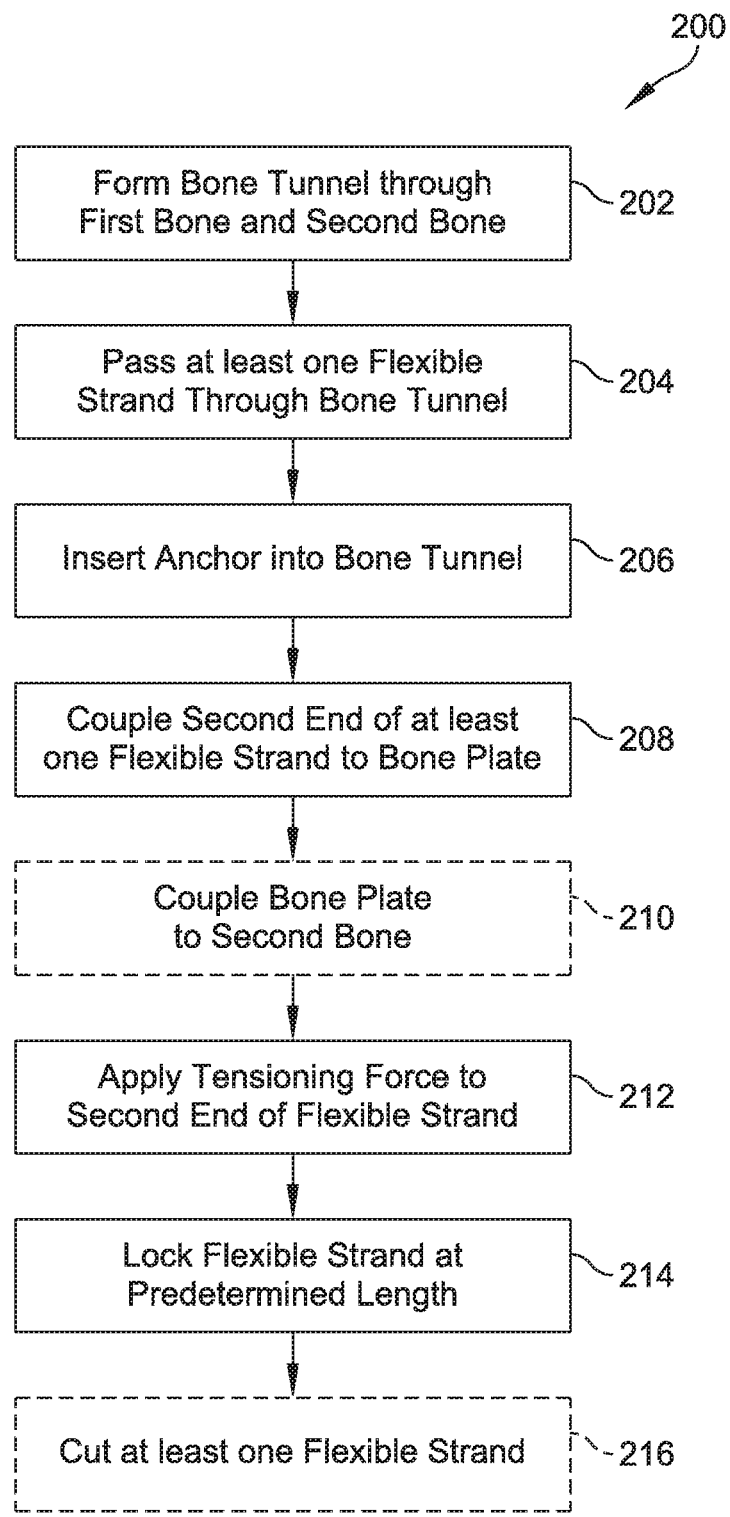
FIG. 8 illustrates a method of syndesmosis, in accordance with some embodiments.

FIG. 8 illustrates a method 200 of syndesmosis, in accordance with some embodiments. At step 202, a bone tunnel 18 is formed through a first bone 4 and a second bone 6. The bone tunnel 18 can include a first portion 20a extending through the first bone and a second portion 20b extending through the second bone 6. The first and second portions 20a, 20b can be aligned along a common longitudinal axis and/or can be offset. The bone tunnel 18 can be formed using any suitable device, such as a drill, needle, k-wire, and/or any other suitable device.

At step 204, at least one flexible strand 16a, 16b is passed through the bone tunnel 18 from a first end corresponding to a surface 4a of the first bone to a second end corresponding to a surface 6a of the second bone 6. In some embodiments, a first end 22a of the at least one flexible strand 16a, 16b is coupled to an anchor 14 and a second end 22b of the flexible strand 16a, 16b is passed through the bone tunnel 18. The anchor 14 includes a body 80 defining a first wing 82a and a second wing 82b coupled at a distal end and each biased away from a longitudinal axis of the body 80. In some embodiments, the anchor 14 includes a coupling extension 94 extending distally from the distal end 92a of the body 80. The coupling extension 94 defines one or more holes 98a, 98b extending therethrough. In some embodiments, each flexible strand 16a, 16b is passed through a selected on of the holes 98a, 98b. A knot or other anchor can be formed at an end of the flexible strand 16a, 16b to couple the flexible strand 16a, 16b to the coupling extension 94.

At step 206, the wings 82a, 82b of the anchor 14 are compressed and the anchor 14 is inserted into the first portion 20a of the bone tunnel 18. In some embodiments, the longitudinal portion 86 of each of the wings 82a, 82b is disposed within the bone tunnel 18 and the transverse portions 90 of each of the wings is disposed against an outer surface 4a of the first bone 4. In some embodiments, the anchor 14 is partially inserted into the first portion 20a of the bone tunnel 18 such the longitudinal portion 86 extends at least partially from the bone tunnel 18.

At step 208, the second end 22b of the flexible strand 16a, 16b is coupled to a strand-locking hole 50 of a bone plate 12. The strand-locking hole 50 includes one or more locking element 62, 64 configured to couple to the flexible strands 16a, 16b. In some embodiments, the flexible strand 16a, 16b can be coupled to the strand-locking hole 50 by passing the flexible strand 16a, 16b from a bone contact surface 32a to an outer surface 32b of the bone plate 12a through the strand-locking hole 50 and beneath the second locking element 64. The flexible strand 16a, 16b is passed back through the strand-locking hole 50 from the outer surface 32b to the bone contacting surface 32a and between the first locking element 62 and the second locking element 64. The flexible strand 16a, 16b is subsequently returned through the strand-locking hole 50 from the bone contacting surface 32a to the outer surface 32b and above the first locking element 62. Although specific embodiments and arrangements of the flexible strands 16a, 16b and the locking elements 62, 64 are discussed herein, it will be appreciated that the flexible strands 16a, 16b can pass through the strand-locking hole 50 and/or interact with the locking elements 62, 64 in any suitable manner and is within the scope of this disclosure.

At optional step 210, the bone plate 12a is coupled to the second bone 6 by one or more fasteners. In some embodiments, one or more locking fasteners are inserted through one or more locking fastener holes 44a-44b, 54a-54b formed in the shaft 40 and/or the head 42 of the bone plate 12a. The one or more locking fasteners are inserted through the locking fastener holes 44a-44b, 54a-54b at a variable angle. The locking fasteners can include any suitable locking fastener, such as a locking fastener having a threaded shaft configured to interface with the second bone 6 and a threaded head configured to lock the locking fastener at a selected angle within the locking fastener hole 44a-44b, 54a-54b. In some embodiments, one or more non-locking fasteners are inserted through one or more non-locking fastener holes 46a-46b formed in the shaft 40 and/or the head 42. The one or more non-locking fasteners compress the bone plate 12 against the outer surface 6a of the second bone. In some embodiments, the non-locking fasteners include a threaded shaft and an unthreaded head, although it will be appreciated that any suitable non-locking fastener can be used. In some embodiments, one or more fasteners are inserted through one or more slots 48 formed through the shaft 40 and/or the head 42. The one or more fasteners can be positioned within a variable location within the slot 48 and coupled to the second bone to compress the bone plate 12a against the second bone 6.

At step 212, a tensioning force is applied to the second end 22b of the at least one flexible strand 16a, 16b to position the first bone 4 and the second bone 6 at a predetermined spacing. The tensioning force advances the second end 22b of the flexible strand 16a, 16b through the strand-locking hole 50 of the bone plate 12. The first end 22a is coupled to the anchor 14 positioned within the bone tunnel 18. The anchor 14 maintains the first end 22a in a fixed position, causing the first bone 4 and the second bone 6 to move towards each other to a predetermined spacing. In some embodiments, the tensioning force causes the anchor 14 to advance into the bone tunnel 18 to a fixed position. In some embodiments, the tensioning force maintains the bone plate 12a in a fixed position with respect to the second bone 6.

At step 214, the at least one flexible strand 16a, 16b is locked at a predetermined length corresponding to a predetermined spacing of the first bone 4 and the second bone 6. In some embodiments, the at least one flexible strand 16a, 16b is locked at the predetermined length by the first locking element 62 and the second locking element 64 disposed within the strand-locking hole 50. For example, in some embodiments, the at least one flexible strand 16a, 16b applies a force to the second locking element 64 during tensioning of the first bone 4 and the second bone 6. When the force applied to the second locking element 64 exceeds a predetermined threshold, the second locking element 64 transitions from a first position (in which the at least one flexible strand 16a, 16b is freely moveable through the strand-locking hole 50) to a second position (in which the at least one flexible strand 16a, 16b is compressed between the first locking element 62 and the second locking element 64). In some embodiments, the compressive force is configured to prevent movement of the at least one flexible strand 16a, 16b through the strand-locking hole 50 and lock the first and second bones 4, 6 at the predetermined spacing.

At optional step 216, the at least one flexible strand 16a, 16b can be cut or otherwise shortened to remove a portion of the at least one flexible strand 16a, 16b extending substantially beyond the outer surface 32b of the bone plate 12. Although specific embodiments are discussed herein, it will be appreciated that the steps of the method 200 can be performed in any suitable order, can be omitted, and/or can be repeated and are within the scope of this disclosure.

Although the devices, kits, systems, and methods have been described in terms of exemplary embodiments, they are not limited thereto. Rather, the appended claims should be construed broadly, to include other variants and embodiments of the devices, kits, systems, and methods, which may be made by those skilled in the art without departing from the scope and range of equivalents of the devices, kits, systems, and methods.

What is claimed is:

1. A system for syndesmosis repair, comprising:
   a bone plate extending between a first surface and a second surface, wherein the bone plate defines a strand-locking hole extending from the first surface to the second surface and oriented along a longitudinal axis of the bone plate;
   a first, fixed locking element and a second locking element that is moveable along the longitudinal axis, each locking element extending from a first side wall that defines the strand-locking hole to a second side wall that defines the strand-locking hole, wherein each of the first locking element and the second locking element extend transverse to the longitudinal axis;
   an anchor comprising a distal end, a first wing and a second wing, wherein the first and second wings are coupled at the distal end and biased away from a longitudinal axis of the anchor, and wherein the first and second wings are configured to maintain the anchor in a fixed position when the anchor is inserted into a hole formed in a bone; and
   a flexible strand coupled to the bone plate and to the anchor.

2. The system of claim 1, wherein a first end of the second locking element is positioned within a first slot defined in the first side wall of the strand-locking hole and a second send of the second locking element is positioned within a second slot defined in the second side wall of the strand-locking hole.

3. The system of claim 1, wherein the second locking element moves along the central axis from a first position to a second position when a predetermined force is applied to the second locking element, wherein the flexible strand is adjustable when the second locking element is in the first position and is locked when the second locking element is in the second position.

4. The system of claim 3, wherein the predetermined force is applied to the second locking element by the flexible strand.

5. The system of claim 1, wherein the anchor comprises a coupling extension extending from the distal end of the first wing and the second wing and defining at least one hole extending therethrough, wherein the at least one hole is sized and configured to receive a flexible strand therethrough.

6. The system of claim 1, wherein the bone plate defines a locking fastener hole extending from the first surface to the second surface.

7. The system of claim 1, wherein the bone plate defines a non-locking fastener hole extending from the first surface to the second surface.

8. The system of claim 1, wherein the bone plate comprises a shaft portion disposed in a first plane, a head portion disposed in a second plane, and an offset portion extending between the shaft portion and the head portion.

9. A method of syndesmosis, comprising:
   forming a bone tunnel through a first bone and a second bone;
   passing at least one flexible strand through the bone tunnel from a first side to a second side, wherein the at least one flexible strand is coupled to an anchor including a body defining a first wing and a second wing, wherein the first and second wings are coupled at a distal end and biased away from a longitudinal axis of the body, and wherein the body is sized and configured for insertion into a first side of the bone tunnel;
   passing the at least one flexible strand through a locking hole formed in a bone plate, wherein the bone plate (i)

is configured to abut a surface of the second bone defining the second side of the bone tunnel and ii comprises a strand-locking hole extending from a first surface to a second surface with a first, fixed locking element and a second locking element that is moveable along a central axis of the strand-locking hole, each locking element extending from a first side wall of the strand-locking hole to a second side wall of the strand-locking hole, wherein each of the first locking element and the second locking element extend transverse to a central axis of the anchor hole;

positioning the first bone and the second bone at a predetermined spacing by applying a tensioning force to the at least one flexible strand; and locking the at least one flexible strand at a predetermined length, wherein the at least one flexible strand is locked by the first locking element and the second locking element.

10. The method of claim 9, wherein insertion of the anchor into the first side of the bone tunnel comprises compressing the first wing and the second wing towards the longitudinal axis.

11. The method of claim 9, wherein passing the at least one flexible strand through the strand-locking hole comprises passing the at least one flexible strand beneath the second locking element, between the first locking element and the second locking element, and above the first locking element.

12. The method of claim 9, wherein the at least one flexible strand is coupled to the anchor by passing the at least one flexible strand through a hole formed in a coupling portion of the anchor and forming a knot in the at least one flexible strand.

13. The method of claim 9, wherein the at least one flexible strand is locked at the predetermined length by transitioning the second locking element from a first position to a second position, wherein the second locking element compresses the at least one flexible strand in the second position.

14. The method of claim 13, wherein the second locking element transitions from the first position to the second position when a predetermined force is applied to the second locking element by the at least one flexible strand.

15. The method of claim 9, coupling the bone plate to the second bone by inserting one or more fasteners through one or more fastener holes formed through the bone plate, wherein the bone plate is coupled to the second bone prior to positioning the first and second bone at a predetermined spacing.

16. The method of claim 15, wherein at least one of the one or more fasteners is a locking fastener and wherein at least one of the one or more fastener holes is a locking hole.

17. A system, comprising:
a bone plate comprising:
    a body extending between a first surface and a second surface, wherein the body defines a strand-locking hole extending from the first surface to the second surface;
    a first, fixed locking element and a second locking element that is moveable along a central axis of the strand-locking hole, each locking element extending from a first side wall of the strand-locking hole to a second side wall of the strand-locking hole, wherein each of the first locking element and the second locking element extend transverse to a central axis of the anchor hole;
an anchor comprising a body defining a first wing and a second wing, wherein the first and second wings are coupled at a distal end and biased away from a longitudinal axis of the body, and wherein the first and second wings are configured to maintain the anchor in a fixed position when the anchor is inserted into a hole formed in a bone, wherein the anchor comprises a coupling extension extending from the distal end of the first wing and the second wing and defining at least one hole extending therethrough; and
a flexible strand extending between the bone plate and the anchor, wherein a first end of the flexible strand is coupled to the at least one hole formed in the coupling extension of the anchor, and wherein a second end of the flexible strand extends beneath the second locking element, between the first locking element and the second locking element, and above the first locking element.

18. The system of claim 17, wherein the first locking element is a fixed locking element and the second locking element is moveable along the central axis of the strand-locking hole.

* * * * *